(12) United States Patent
Obara

(10) Patent No.: US 7,169,177 B2
(45) Date of Patent: Jan. 30, 2007

(54) BIFURCATED STENT

(75) Inventor: Robert Z. Obara, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 71 days.

(21) Appl. No.: 10/342,756

(22) Filed: Jan. 15, 2003

(65) Prior Publication Data

US 2004/0138736 A1    Jul. 15, 2004

(51) Int. Cl.
A61F 2/06    (2006.01)
(52) U.S. Cl. ..................... 623/1.35; 623/1.15
(58) Field of Classification Search ............... 623/1.35
See application file for complete search history.

(56) References Cited

U.S. PATENT DOCUMENTS

| | | | |
|---|---|---|---|
| 4,733,665 A | 3/1988 | Palmaz | 128/343 |
| 4,994,071 A | 2/1991 | MacGregor | 606/194 |
| 5,383,892 A | 1/1995 | Cardon et al. | 606/198 |
| 5,607,444 A | 3/1997 | Lam | 606/194 |
| 5,632,763 A | 5/1997 | Glastra | 606/194 |
| 5,669,924 A | 9/1997 | Shaknovich | 606/108 |
| 5,676,697 A | 10/1997 | McDonald | 623/1 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,824,052 A | 10/1998 | Khosravi et al. | 623/1 |
| 5,827,320 A | 10/1998 | Richter et al. | 606/194 |
| 5,833,707 A | 11/1998 | McIntyre et al. | 606/198 |
| 5,868,777 A | 2/1999 | Lam | 606/194 |
| 5,906,640 A | 5/1999 | Penn et al. | 623/1 |
| 6,017,363 A | 1/2000 | Hojeibane | 623/1 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,086,611 A | 7/2000 | Duffy et al. | 623/1 |
| 6,117,156 A | 9/2000 | Richter et al. | 606/194 |
| 6,224,609 B1 | 5/2001 | Ressemann et al. | 606/108 |
| 6,251,133 B1 | 6/2001 | Richter et al. | 623/1.16 |
| 6,319,278 B1 | 11/2001 | Quinn | 623/1.13 |
| 6,344,056 B1 | 2/2002 | Dehdashtian | 623/1.35 |
| 6,361,544 B1 | 3/2002 | Wilson et al. | 606/194 |
| 6,406,489 B1 | 6/2002 | Richter et al. | 623/1.16 |
| 6,428,567 B2 | 8/2002 | Wilson et al. | 623/1.11 |

(Continued)

FOREIGN PATENT DOCUMENTS

DE    199 06 956 A1  *  8/2000

(Continued)

Primary Examiner—Tom Barrett
(74) Attorney, Agent, or Firm—Vidas, Arrett, Steinkraus

(57) ABSTRACT

A bifurcated stent comprises a body portion, a first branch portion, a second branch portion, a first pivot portion and a second pivot portion constructed from a common continuous sheet of stent material. The body portion, first branch portion and second branch portion provided with a substantially tubular shape, the tubular shape of each defines a lumen respectively therethrough. The lumen defined by the body portion is in fluid communication with the lumen defined by the first branch portion and the second branch portion. The first branch portion is pivotally engaged to an end of the body portion by the first pivot portion. The second branch portion is pivotally engaged to an end of the body portion by the second pivot portion.

25 Claims, 4 Drawing Sheets

U.S. PATENT DOCUMENTS

| | | | |
|---|---|---|---|
| 6,436,134 B2 | 8/2002 | Richter et al. | 623/1.15 |
| 6,461,380 B1 | 10/2002 | Cox | 623/1.17 |
| 6,478,813 B1 | 11/2002 | Keith et al. | 623/1.11 |
| 2002/0193873 A1* | 12/2002 | Brucker et al. | 623/1.35 |

FOREIGN PATENT DOCUMENTS

| | | |
|---|---|---|
| DE | 101 05 160 A1 | 8/2002 |
| WO | 99/02092 | 1/1999 |
| WO | 99/40873 | 8/1999 |
| WO | 99/65418 | 12/1999 |
| WO | WO 00/13613 * | 3/2000 |
| WO | WO 01/35715 A2 * | 5/2001 |

* cited by examiner

BIFURCATED STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding or expanded by an internal radial force, such as when mounted on a balloon.

Stents are generally tubular devices for insertion into body lumens. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

Stents may be constructed from a variety of materials such as stainless steel, Elgiloy, nitinol, shape memory polymers, etc. Stents may also be formed in a variety of manners as well. For example a stent may be formed by etching or cutting the stent pattern from a tube or section of stent material; a sheet of stent material maybe cut or etched according to a desired stent pattern whereupon the sheet may be rolled or otherwise formed into the desired tubular or bifurcated tubular shape of the stent; one or more wires or ribbons of stent material may be braided or otherwise formed into a desired shape and pattern.

A stent may be used to provide a prosthetic intraluminal wall e.g. in the case of a stenosis to provide an unobstructed conduit for blood in the area of the stenosis. An endoluminal prosthesis comprises a stent which carries a prosthetic graft layer of fabric and is used e.g. to treat an aneurysm by removing the pressure on a weakened part of an artery so as to reduce the risk of embolism, or of the natural artery wall bursting. Typically, a stent or endoluminal prosthesis is implanted in a blood vessel at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to re-expand to a predetermined diameter in the vessel.

Within the vasculature however it is not uncommon for stenoses to form at any of a wide variety of vessel bifurcations. A bifurcation is an area of the vasculature or other portion of the body where a first (or parent) vessel is bifurcated into two or more branch vessels. Bifurcations exist within the body in a wide variety of configurations, angles, and vessel diameters. Where a stenotic lesion or lesions form at such a bifurcation, the lesion(s) can affect only one of the vessels (i.e., either of the branch vessels or the parent vessel) two of the vessels, or all three vessels.

Unfortunately however, many prior art stents are not wholly satisfactory for use where the site of desired application of the stent is juxtaposed or extends across a bifurcation, particularly the carina of the bifurcation. Many current stent designs are unsuited for directing blood flow around and/or away from an aneurism located at or adjacent to the carina of a bifurcation. Moreover, many of the currently available stent designs are incapable of being implanted into various configurations and sizes of bifurcations within a body without out extensive pre-implantation modification, if at all.

Thus, there remains a need for a bifurcated stent that may be utilized in a wide variety of vessel bifurcations, without requiring that the stent be extensively modified prior to implantation, and to provide a stent that is capable of fully supporting the carina of a vessel bifurcation while still being capable of deflecting blood from a lesion located at or around the carina and/or diverting blood around the carina.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention includes many different embodiments. For example in at least one embodiment, the invention is directed to a bifurcated stent constructed from a sheet of suitable material and formed into three main sections, wherein two of the sections, or branches, are pivotally engaged to the third section, or body, of the stent.

In some embodiments the stent, one or more individual stent sections or one or more portions thereof may be balloon expandable, self-expandable, or hybrid expandable.

In at least one embodiment the stent is constructed from at least one sheet of nickel, titanium, nickel-titanium alloys such as nitinol, stainless steel and alloys thereof, tantalum, or other suitable material. The at least one sheet is etched, cut or otherwise provided with a suitable stent pattern of interconnected strut members.

In some embodiments the individual sections of the stent are each formed by rolling or joining two opposing sides of a respective section of the sheet into a substantially tubular form. The substantially tubular shape of each section may be retained together by engaging the opposing side of the sheet along a joining seam. The opposing sides may be joined by chemical or physical adhesion, welding, through the use of external ties, or fasteners, or by any type of engagement mechanism desired. In some embodiments the opposing sides of the sheet section are at least partially overlapped and remain free to move relative to one another. Whether the sections are joined at a seam or are free to move relative to one another, the individual sections of the stent may be independently expandable between at least an unexpanded state, an expanded state and/or one or more diameters therebetween.

In some embodiments, each branch of the stent is engaged to the body at a pivot connection. The pivot connection between each branch portion of the stent and the body portion of the stent comprises at least one strut member. In at least one embodiment the pivotal connections are each defined by a portion of the sheet which has a circumferential length less than that of either branch or the body portion of the stent. The pivot connections provide a pivot point between each branch and the stent body to allow the stent to accommodate a variety of bifurcation angles and configurations.

In some embodiments the design or pattern of struts provided to the walls of each branch of the stent (via the etching or cutting of the sheet from which the stent sections are formed) is varied in density to provide one or more regions which are less porous, have a greater concentration of struts or stent material and/or define holes that are fewer in number and/or smaller than adjacent portions of the stent section. This "denser region" is constructed and arranged to overlay a lesion located at or around the carina of the bifurcation. The denser region of the sections may be configured to prevent or reduce blood from reaching the lesion site so that blood passing through the stent branches is directed around the bifurcation.

In some embodiments one or more of the branches may be provided with one or more aneurysm flaps on the external surface of the branch which is to be immediately adjacent to the carina and/or inside surface of the vessel bifurcation. The flaps are constructed and arranged to divert blood flow away from and around the aneurysm or lesion site.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the drawings.

DETAILED DESCRIPTION OF THE INVENTION

As indicated above the present invention includes many different embodiments. In some embodiments the invention is directed to various designs of bifurcated stents and their methods of manufacture and use.

Figure 1:
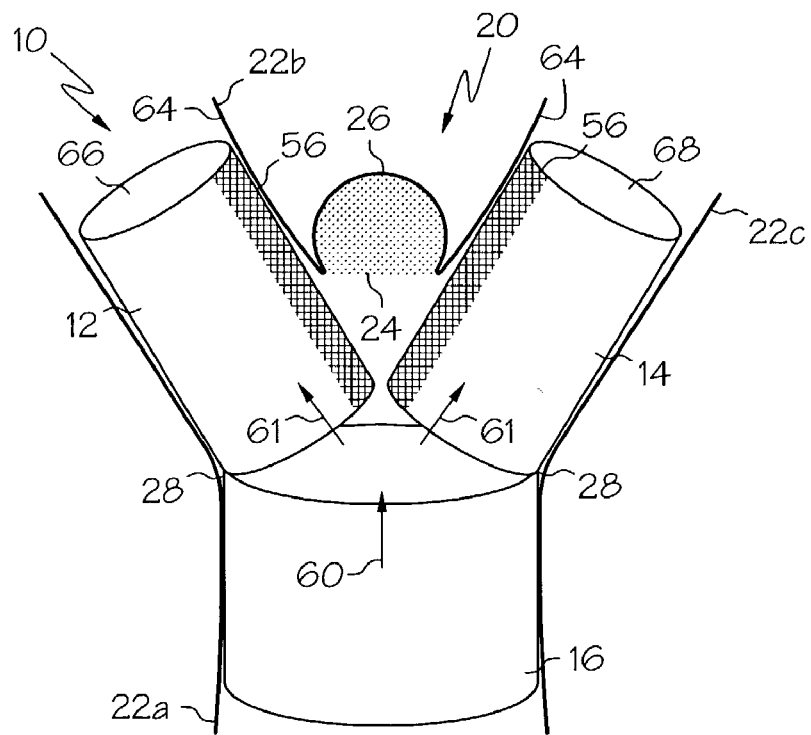
FIG. 1 is a cross-sectional longitudinal side view of an embodiment of the invention positioned at a bifurcation of vessels.
Figure 2:
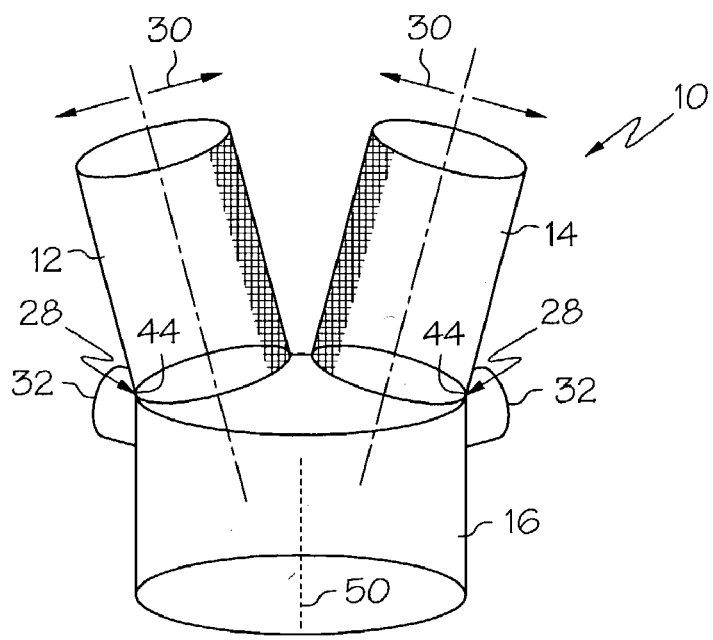
FIG. 2 is a perspective view of the embodiment of FIG. 1.

In at least one embodiment, the invention is directed to a bifurcated stent, indicated generally at 10 in FIGS. 1 and 2, having three main sections, wherein two of the sections, or branches 12 and 14, are pivotally engaged to the third section, or body 16, of the stent 10.

In use, stent 10 may be advanced to a bifurcation 20 of vessels 22 by any delivery mechanism or device known such as one or more stent delivery catheters (not shown) that may be capable if independently positioning each of the branches 12 and 14 as well as the body 16 within one or more vessels 22, such as is shown in FIG. 1. The stent 10 or one or more portions of one or more of the sections 12, 14 and 16 may be balloon expandable, self-expandable, and/or hybrid expandable as desired.

As is discussed in greater detail below, the branches 12 and 14 are flexibly or pivotally engaged to the body 16 at one or more pivot connections 28. As indicated by arrows 30 in FIG. 2, the individual branches 12 and 14 may be pivotally positioned relative to body 16, to form an angle 32 with the body of about 0 degrees to about 180 degrees. In some embodiments the branches may be pivoted to form angles with the body 16 of about 0 to about 90 degrees. By providing the stent 10 with pivot connections 28, the branches 12 and 14 may be positioned into a wide variety of bifurcation configurations that may be found with a human or mammalian anatomy.

As illustrated in FIG. 1, once the stent 10 is advanced to the bifurcation 20, the branches 12 and 14 are each positioned for deployment so as to extend from the main vessel 22*a* and into one of the side vessels 22*b* or 22*c* respectively. The flexible connection between the body 16 and each branch 12 and 14 allows each branch to be positioned into the respective side vessel regardless of the angle that the side vessel 22*b* and 22*c* forms with the main vessel 22*a*. In at least one embodiment, the branches 12 and 14 are configured to at least partially surround a lesion 26 located at or around the carina 24 of the bifurcation 20. If desired the stent may be positioned such that the branches 12 and 14 are immediately engaged to the carina 24 or lesion 26 positioned thereon or adjacent thereto.

Figure 3:
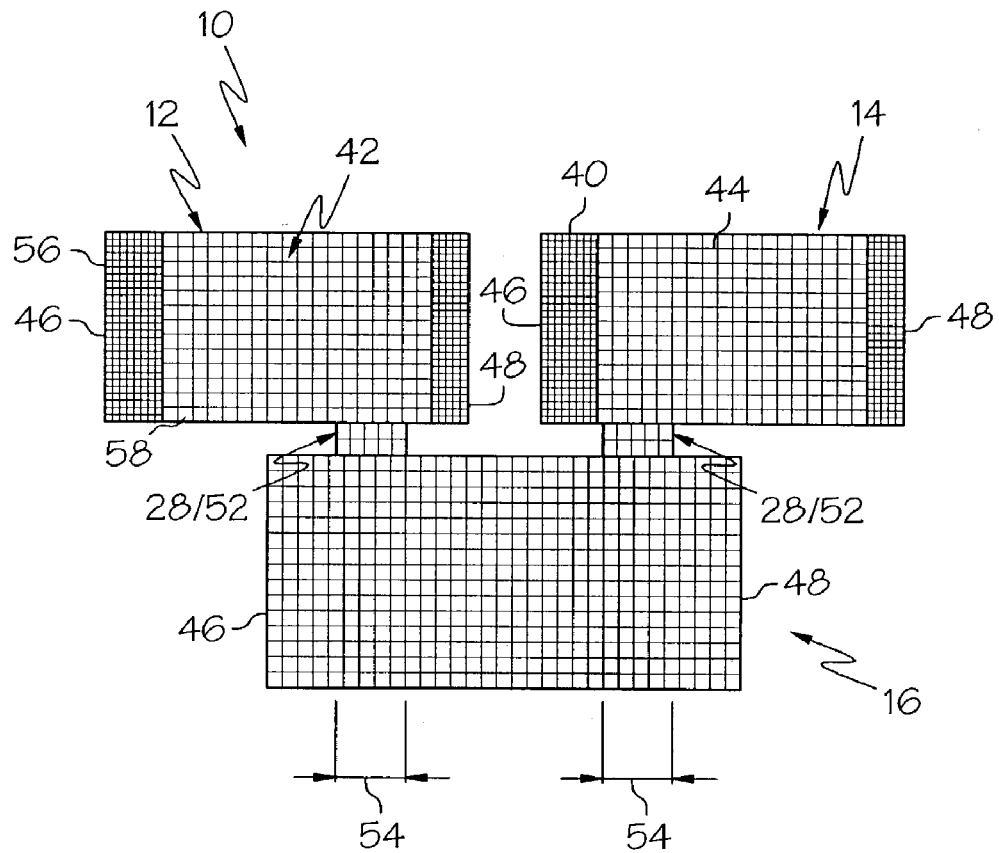
FIG. 3 is a top down view of a sheet for use in constructing the embodiment of FIG. 2.

In at least one embodiment, an example of which is illustrated in FIG. 3, the stent 10 of FIGS. 1 and 2 is constructed from at least one sheet 40 of nickel, titanium, nickel-titanium alloys such as nitinol, stainless steel and alloys thereof, tantalum, or other suitable material for constructing a stent. If desired one or more portions of the stent may be made more or less radiopaque depending on the material from which the stent 10 is constructed. In some embodiments the stent 10 comprises one or more radiopaque markers or marker bands.

The at least one sheet 40 is etched, cut or otherwise provided with a suitable stent pattern 42 of interconnected strut members 44.

Figure 4:
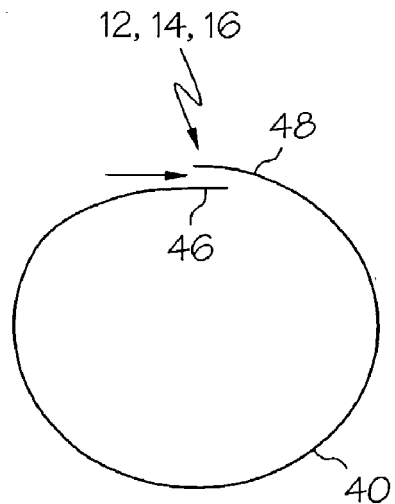
FIG. 4 is a cross-sectional view of a portion of the sheet shown in FIG. 3 formed into a tubular section of the stent of FIG. 2 wherein the opposing sides of the sheet portion are overlappingly engaged.
Figure 5:
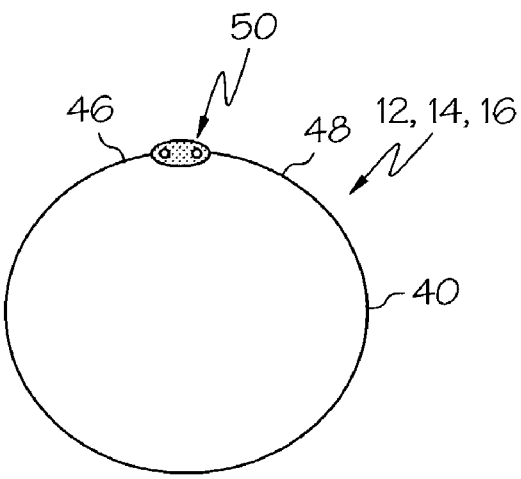
FIG. 5 is a cross-sectional view of a portion of the sheet shown in FIG. 3 formed into a tubular section of the stent of FIG. 2 wherein the opposing sides of the sheet portion are engaged along a seam.

In at least one embodiment the individual sections 12, 14 and/or 16 of the stent 10 are formed by rolling or joining two opposing sides 46 and 48 of a respective section 12, 14 and/or 16 of the sheet 40 into a substantially tubular form such as illustrated in FIGS. 4 and 5. In the embodiment shown in FIG. 5, the substantially tubular shape of each section 12, 14 and/or 16 may be retained by engaging the opposing side 46 and 48 of the sheet 40 together along a joining seam 50. The seam 50 may comprise a chemical or physical adhesive, weld, one or more external ties or fasteners, or any type of engagement mechanism desired.

Alternatively, in the embodiment shown in FIG. 4 the opposing sides 46 and 48 of the sheet 40 of the desired section 12, 14 and/or 16 are at least partially overlapped or coiled but remain free to move and expand relative to one another.

Whether the sections 12, 14 and/or 16 of the resulting stent 10, such as is shown FIG. 2 are joined at a seam 50, as shown in FIG. 5, or are free to move relative to one another, as shown in FIG. 4, the individual sections 12, 14 and/or 16 of the stent 10 may be independently expandable between at least an unexpanded state, an expanded state and/or one or more diameters therebetween by any manner such as is known in the art.

In the stent 10 shown in FIG. 2, the pivot connection 28 between each branch portion 12 and 14 of the stent 10 and the body portion 16 of the stent 10 comprises at least one strut member 44 of the sheet 40 shown in FIG. 3. In some embodiments however, a pivot connection 28 may be comprised of a connector portion 52 of the sheet 40 which extends between the body 16 and the respective branch 12 and 14 and defines a planar or circumferential length 54 less than that of any of the sections 12, 14, and 16 of the sheet 40.

Figure 6:
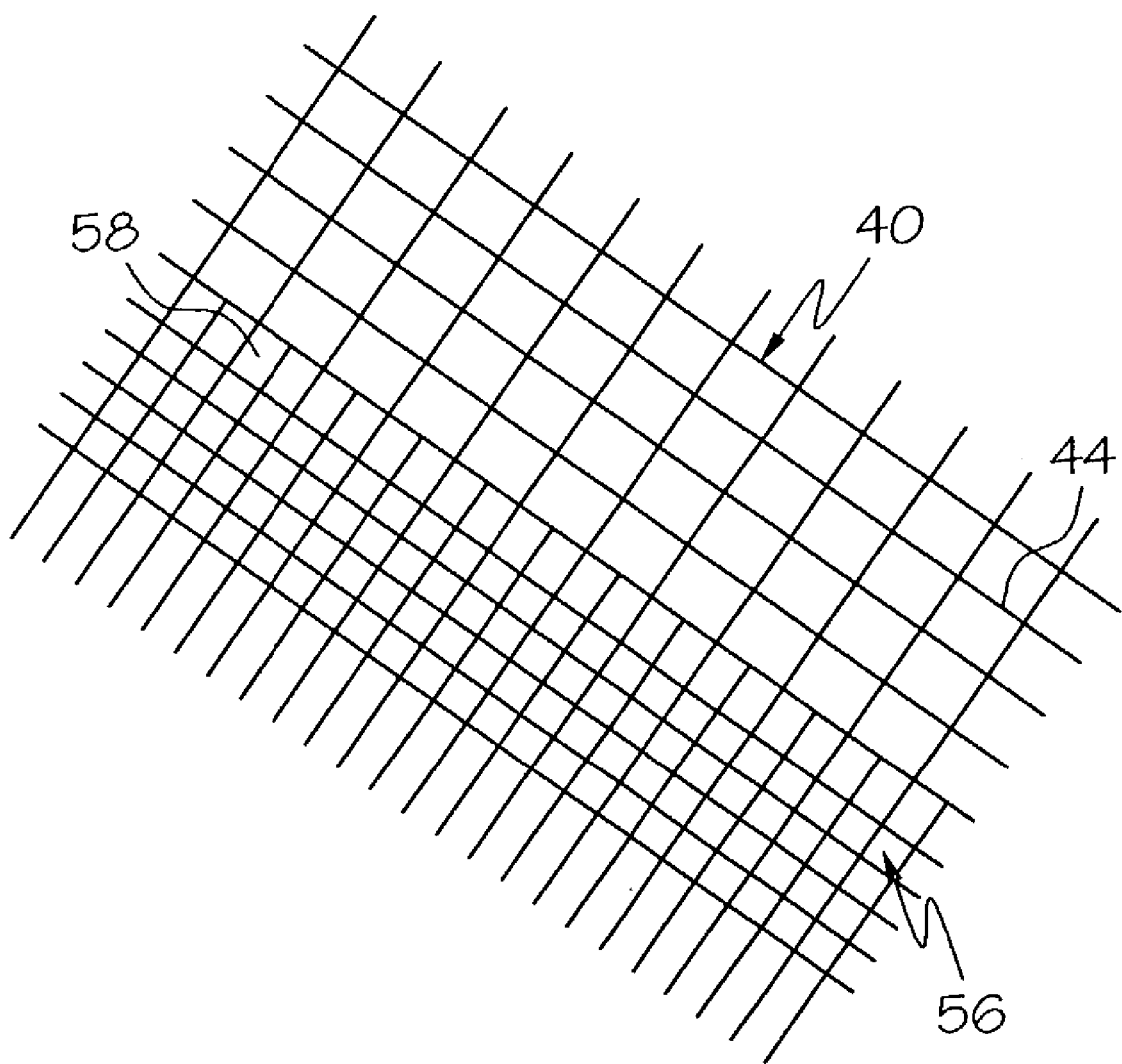
FIG. 6 is a partial side view of an embodiment wherein at least a portion of the sheet for constructing a bifurcated stent defines a pattern of at least two different densities of stent material.

In some embodiments the design or pattern 42 of struts 44 provided to the sections 12, 14 and/or 16 of the stent 10 by the etching, cutting or other processing of the sheet 40 shown in FIG. 3 is varied in density to provide one or more regions 56 which are less porous, have a greater concentration of struts 44 or stent material and/or define holes 58 that are fewer in number and/or smaller than adjacent portions of the respective stent section, such as in the manner shown in FIG. 6. Such "denser regions" 56 are constructed and arranged to overlay or be positioned against the lesion 26 located at or around the carina 24 of the bifurcation 20, as shown in FIG. 1. The denser region 56 of the branch sections 12 and 14 are configured to prevent or reduce blood flow, indicated by arrows 60 and 61, from reaching the lesion 26 so that the blood passing through the stent sections 12, 14 and 16 is directed around the bifurcation 20.

Figure 7:
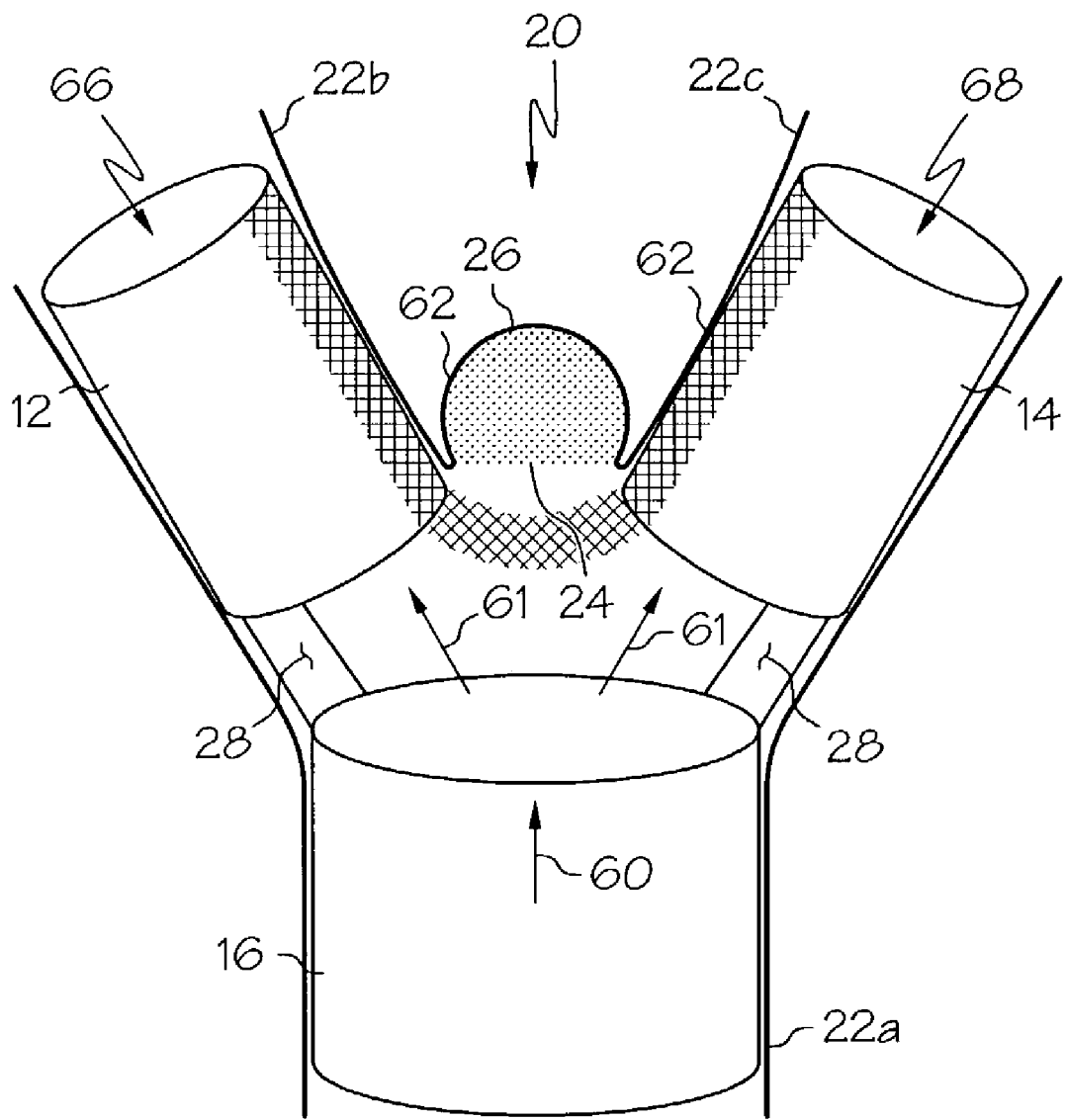
FIG. 7 is a perspective view of the embodiment of FIG. 1 wherein the stent is equipped with aneurysm flaps.

In some embodiments, an example of which is illustrated in FIG. 7, one or more of the branches 12 an 14 may be provided with one or more aneurysm flaps 62 on the external surface of the branch 12 and/or 14 which is to be immediately adjacent to the carina 24 and/or inside surface 64 of the vessel branches 22b and 22c. The flaps 62 are constructed and arranged to overlap one another to close the lumens 66 and 68 defined by each branch 12 and 14, respectively, from the aneurysm or lesion site 26. In order to provide the flaps 62 with the ability to overlappingly engage one another, the flaps 62, or a portion thereof may be constructed from a shape-memory material which, when allowed to transition to a memorized shape upon implantation of the stent 10, causes the flaps 62 to bend toward and/or around the carina 24 of the bifurcation 20.

In some embodiments the flaps 62 may be characterized as pivot connections 28, such as have been previously described, but which are engaged only to branches 12 and 14, respectively, and are not engaged to the body 16. The flaps 62 are moveable or pivotable between an open position wherein blood or other fluid is free to access the lesion 26 and a closed position shown wherein the flow of blood 60 and 61 is diverted around the lesion 26.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A bifurcated stent comprising:

a body portion, a first branch portion, a second branch portion, a first pivot portion and a second pivot portion; the body portion, the first branch portion, the second branch portion, the first pivot portion and the second pivot portion constructed from a common continuous sheet of stent material, each of the body portion, first branch portion and second branch portion having a first side and a second side opposite the first side and fixedly engaged to the first side to provide each of the body portion, first branch portion and second branch portion with a substantially tubular shape and defining a lumen respectively therethrough, the lumen defined by the body portion being in fluid communication with the lumen defined by the first branch portion and the second branch portion, the first branch portion being pivotally engaged to an end of the body portion by the first pivot portion, the second branch portion being pivotally engaged to an end of the body portion by the second pivot portion;

at least one of the first branch portion and the second branch portion comprising at least one aneurysm flap, the at least one aneurysm flap constructed and arranged to be positioned immediately adjacent to a carina of a vessel bifurcation.

2. The bifurcated stent of claim 1 wherein at least a portion of at least one of the body portion, the first branch portion and the second branch portion constructed and arranged to be balloon expandable, self-expandable or hybrid expandable.

3. The bifurcated stent of claim 1 wherein the first branch portion defines an angle with the body portion, the angle being about 0 degrees to about 180 degrees.

4. The bifurcated stent of claim 1 wherein the first branch portion defines an angle with the body portion, the angle being about 0 degrees to about 90 degrees.

5. The bifurcated stent of claim 1 wherein the second branch portion defines an angle with the body portion, the angle being about 0 degrees to about 180 degrees.

6. The bifurcated stent of claim 1 wherein the first branch portion and the second branch portion are constructed and arranged to at least partially engage the carina of the vessel bifurcation.

7. The bifurcated stent of claim 1 wherein the sheet of stent material is at least partially constructed form at least one material of the group consisting of: nickel, titanium, nickel-titanium alloys, stainless steel, stainless steel alloys, tantalum and any combinations thereof.

8. The bifurcated stent of claim 1 wherein the sheet of stent material defines a pattern of interconnected strut members, wherein adjacent interconnected strut members define openings therethrough.

9. The bifurcated stent of claim 8 wherein the pattern of interconnected struts defines at least one first area of interconnected strut members and at least one second area of interconnected strut members the at least one first area having a greater density of stent material than the at least one second area.

10. The bifurcated stent of claim 9 wherein the first branch portion and the second branch portion are each at least partially defined by the at least one first area and the at least one second area.

11. The bifurcated stent of claim 10 wherein the first branch portion and the second branch portion are constructed and arranged to at least partially engage a vessel bifurcation, when the first branch portion and the second branch portion are at least partially engaged to the vessel bifurcation the at least one first area of the first branch portion and the second branch portion is positioned immediately adjacent to the carina of the vessel bifurcation.

12. The bifurcated stent of claim 1 wherein the sheet of stent material defines a body section, a first branch section and a second branch section, the body section constructed and arranged to be formed into the body portion, the first branch section constructed and arranged to be formed into the first branch portion and the second branch section constructed and arranged to be formed into the second branch portion.

13. The bifurcated stent of claim 12 wherein the body section of the sheet defines a first body section end and a second body section end, the body portion being provided with the substantially tubular shape by engaging the first body section end and the second body section end one to the other.

14. The bifurcated stent of claim 13 wherein the first body section end and the second body section end are at least partially overlappingly engaged one to the other.

15. The bifurcated stent of claim 12 wherein the first branch section of the sheet defines a first branch section end and a second first branch section end, the first branch portion being provided with the substantially tubular shape by engaging the first branch section end and the second branch section end one to the other.

16. The bifurcated stent of claim 15 wherein the first branch section end and the second branch section end are at least partially overlappingly engaged one to the other.

17. The bifurcated stent of claim 12 wherein the second branch section of the sheet defines a first branch section end and a second branch section eud, the second branch portion being provided with the substantially tubular shape by engaging the first branch section end and the second branch section end one to the other.

18. The bifurcated stent of claim 17 wherein the first branch section end and the second branch section end are at least partially overlappingly engaged one to the other.

19. The bifurcated stent of claim 8 wherein each of the first pivot connection and the second pivot connection comprise at least one strut member.

20. The bifurcated stent of claim 1 wherein the first pivot connection is defined by a section of the sheet of stent material extending between the body portion and the first branch portion when the body portion and the first branch portion are respectively provided with the substantially tubular form, the first pivot connection having a circumferential length less than that of the body portion and the first branch portion.

21. The bifurcated stent of claim 1 wherein the second pivot connection is defined by a section of the sheet of stent material extending between the body portion and the second branch portion when the body portion and the second branch portion are respectively provided with the substantially tubular form, the second pivot connection having a circumferential length less than that of the body portion and the second branch portion.

22. The bifurcated stent of claim 1 wherein the at least one aneurysm flap is constructed of a shape memory material.

23. The bifurcated stent of claim 22 wherein the at least one aneurysm flap comprises a first aneurysm flap and a second aneurysm flap, the first aneurysm flap being pivotally engaged to only the first branch portion, the second aneurysm flap being pivotally engaged to only the second branch portion.

24. The bifurcated stent of claim 23 wherein the first aneurysm flap and the second aneurysm flap are each moveable from a open position and a closed position, in the closed position the first aneurysm flap and the second aneurysm flap being overlappingly engaged to one another over the carina of the vessel bifurcation.

25. A method of manufacturing a bifurcated stent comprising the steps of:

providing a single sheet of stent material with a body section, the body section having a primary body end and a secondary body end; a first branch section, the first branch section having a primary first branch end and a secondary first branch end; a second branch section, the second branch section having a primary second branch end and a secondary second branch end; a first connector section; and a second connector section wherein the first connector section extends between a first end of the body section to an adjacent end of the first branch section, and the second connector section extends between the first end of the body section to an adjacent end of the second branch section; at least one of the adjacent end of the first branch section and the adjacent end of the second branch section comprising at least one aneurysm flap, the at least one aneurysm flap constructed and arranged to be positioned immediately adjacent to a carina of a vessel bifurcation;

providing the single sheet of stent material with a predetermined pattern of interconnected struts and openings defined therebetween, each of the first connector section and the second connector section comprising at least one interconnected strut;

engaging the primary body end and the secondary body end one to the other to provide a body portion of the stent;

engaging the primary first branch end and the secondary first branch end one to the other to provide a first branch portion of the stent; and engaging the primary second branch end and the secondary second branch end one to the other to provide a second branch portion of the stent.

* * * * *